United States Patent [19]

Kondo et al.

[11] Patent Number: 4,472,262

[45] Date of Patent: Sep. 18, 1984

[54] LIMITING ELECTRIC CURRENT TYPE OXYGEN CONCENTRATION DETECTOR APPLIED WITH TEMPERATURE COMPENSATION

[75] Inventors: Haruyoshi Kondo; Keiichi Saji; Takashi Takeuchi; Yasuhiro Otsuka; Toshinobu Furutani; Mari Okazaki, all of Aichi, Japan

[73] Assignees: Kabushiki Kaisha Toyota Chuo Kenkyusho; Toyota Judosha Kogyo Kabushiki Kaisha, both of Aichi, Japan

[21] Appl. No.: 381,025

[22] Filed: May 24, 1982

[30] Foreign Application Priority Data

May 25, 1981 [JP] Japan ................................ 56-78028

[51] Int. Cl.$^3$ .................... G01N 27/56; G01N 27/58; G01N 27/30
[52] U.S. Cl. ................................ 204/408; 204/425; 204/426; 204/1 T; 204/429
[58] Field of Search .................... 204/195 S, 1 S, 1 T, 204/195 R, 1 Y, 406, 408, 421, 424, 426, 429, 431, 432, 425; 123/440, 489, 589; 60/276; 364/497

[56] References Cited

U.S. PATENT DOCUMENTS

| | | | |
|---|---|---|---|
| 4,187,806 | 2/1980 | Schnurle et al. | 60/276 |
| 4,207,159 | 6/1980 | Kimura et al. | 123/440 |
| 4,245,314 | 1/1981 | Henrich et al. | 60/276 |
| 4,263,652 | 4/1981 | Henrich | 60/276 |
| 4,263,883 | 4/1981 | Treible et al. | 60/276 |
| 4,365,604 | 12/1982 | Sone | 204/1 S |
| 4,366,039 | 12/1982 | Uchida et al. | 204/195 S |
| 4,376,026 | 3/1983 | Hoffman et al. | 204/408 |
| 4,391,691 | 7/1983 | Linder et al. | 204/426 |

*Primary Examiner*—T. Tung
*Assistant Examiner*—B. J. Boggs, Jr.

[57] ABSTRACT

An oxygen concentration detector provided with an oxygen concentration sensor further provided with an oxygen ionic conductor, a cathode placed on one surface of the oxygen ionic conductor, an anode placed on the other surface of the oxygen ionic conductor, and a layer convering the cathode for regulating the diffusion of oxygen gas toward the cathode. Temperature compensation is applied to the output of the detector which is inherently influenced by the temperature of the sensor. More specifically, an oxygen concentration detector is provided with the foregoing oxygen concentration sensor, and voltage or current is alternatively supplied to the sensor to measure a limiting current of the sensor and internal resistance of the sensor, and the current or the voltage produced by the foregoing application of voltage or current, and a temperature compensation is applied to the detected magnitude of limiting current according to the internal resistance of the sensor.

12 Claims, 13 Drawing Figures

LIMITING ELECTRIC CURRENT TYPE OXYGEN CONCENTRATION DETECTOR APPLIED WITH TEMPERATURE COMPENSATION

BACKGROUND OF THE INVENTION

1. Field of the Invention

The present invention relates to equipment employable for detecting the concentration of oxygen contained in a gas, and more particularly to a limiting electric current type oxygen concentration detector which is provided with a temperature compensation means which applies temperature compensation to results of measurement for the concentration of oxygen contained in a gas.

The oxygen concentration detector in accordance with the present invention is employable for detecting the oxygen concentration contained in exhaust gases emitted by a boiler installed in thermal power stations, internal combustion engines mounted on automobiles.

2. Statement of the Prior Art

Needless to emphasize, various types of combustion equipment such as boilers installed in thermal power-stations, internal combustion engines and the like are presently available and they are means essential for modern social life in various aspects.

However, such equipment is inevitably accompanied by a possibility of emission of a considerable quantity of injurious gases, depending on the condition on which such combustion equipment operates or the condition on which the combustion takes place. Further, a strong requirement has come out for development of combustion equipment which requires less fuel consumption.

It is believed that combustion in an atmosphere containing a lesser quantity of a fuel (Hereinafter referred to as an air-fuel mixture or lean mixture) is possibly effective to simultaneously satisfy both the requirements to decrease the quantity of injurious gases contained in exhaust gases and to decrease the quantity of fuel used for generation of a unit quantity of energy. For example, it is publicly known that a lean mixture is preferably employed for a Diesel engine. Therefore, it is hopefully assumed that a lean mixture could be employed also for a gasoline engine to satisfy the foregoing objects.

However, a mixture containing a fuel and air in an undesirable ratio readily causes such engines to exhaust a considerable quantity of soot and/or causes misfiring, despite the fact that such engines inherently prefer lean mixture, resulting various problems including air pollution due to emission of soot or unburned fuel and less satisfactory combustion efficiency. In other words, such a misuse of a lean mixture is not only ineffective to satisfy the foregoing objects but also is involved with the possibility of causing various reverse effects. Therefore, adjustment of the ratio of fuel and air is an extremely important parameter to enable combustion equipment to operate under satisfactory conditions under which it is allowed to exhibit the expected performance. It is quite true for any type of control system that the accurate and quick detection of an object to be controlled (In this case, this object is the ratio of a mixture, and air in a lean fuel more specifically, the oxygen concentration in the exhaust gas.) is essential for performance of the control system. Unfortunately, however, none of the sensors which are at present available in the prior art is satisfactory for such purposes. For example, the magnetic oxygen concentration detector is unsatisfactory for the purpose to be employed under a condition wherein the detector is mounted on an automobile, because of its rather slow response speed. The density type sensor or thermal conductivity type sensor is also unsatisfactory for the purpose to control combustion of an internal combustion engine, because the accuracy thereof is inclined to be adversely influenced by a marginal quantity of hydrogen ($H_2$) contained in a gas.

One piece of equipment for detecting oxygen concentration in accordance with the prior art is represented by a sensor employable for detecting limiting electric current for the purpose of analyzing oxygen concentration in a gas (Hereinafter, referred to as "a limiting electric current type oxygen concentration sensor"), the sensor being invented by the inventors of the present invention and was laid open to the public inspection under the laying-open of Application No. Toku-Kai-Sho No. 52-72286 in Japan and which disclosed the conceptual construction of the limiting electric current type oxygen concentration detector, and by another limiting electric current type oxygen concentration sensor which was invented by the inventors of the present invention and was filed under Application No. Toku-Gan-Sho No. 55-123677 in Japan which disclosed an improvement applied to the foregoing conceptual construction or an improved construction of a limiting electric current type oxygen concentration sensor of which the cathode is covered by a porous material layer.

Either of these limiting current type oxygen concentration sensors is free from various drawbacks which inevitably are involved with the oxygen concentration detectors available in the prior art. From this view point, either of these limiting current type oxygen concentration sensors is recognized as oxygen concentration sensor having an excellent features. From other viewpoints, particularly in the realistic aspects, however, either of the foregoing limiting current type oxygen concentration sensors is involved with possibilities of further improvements. It is quite often that internal combustion engines mounted on vehicles vary the temperature of their exhaust gases depending on the corresponding operating conditions. Therefore, a limiting current type oxygen concentration sensor is required to have a stable performance in a relatively wide range of temperature, when it is employed as a sensor for the exhaust gas of engines whose operation rates frequently vary e.g. engines mounted on vehicles. However, the limiting current type oxygen concentration sensors available in the prior art are accompanied by two drawbacks including (1) that the internal resistance of the sensor varies over a wide range depending on the temperature thereof, and (2) that the limiting electric current vs. oxygen concentration relations vary according to the temperature thereof, these drawbacks, in combination, resulting in an error of measurement of the oxygen concentration.

OBJECTS AND SUMMARY OF THE INVENTION

An object of the present invention is to obviate the first of the drawbacks described above, and to provide a limiting electric current type oxygen concentration detector wherein an improvement is realized to prevent the undesirable results caused by the foregoing variation of the oxygen concentration vs. limiting current relations from occurring depending on the temperature of the foregoing sensor.

Another object of the present invention is to provide a limiting electric current type oxygen concentration sensor wherein improvements are realized (1) that a correction is applied to the measurement error caused by the inherent nature of such a sensor which varies the oxygen concentration vs. limiting current relations according to the temperature thereof, (2) that the restriction is removed for a temperature range in which the measurement is allowed for the oxygen concentration, (3) that the magnitude of the measurement accuracy is increased and (4) that the sensor is allowed to be applied over a wider temperature range of measurement of the oxygen concentration.

To achieve the foregoing objects, a limiting electric current type oxygen concentration detector in accordance with the present invention is provided with (a) a limiting electric current type oxygen concentration sensor, (b) a first means for electrically driving the foregoing limiting electric current type oxygen concentration sensor for the purpose of measuring the limiting current and the internal resistance thereof, (c) a second means for measuring a limiting current flowing in the foregoing sensor and for measuring the electrical quantity of the foregoing sensor which is proportional to the internal resistance thereof, by means of electrical driving of the foregoing first means, (d) a third means for allocating time to a first period in which the foregoing limiting current is allowed to be measured and a second period in which the foregoing internal resistance is allowed to be measured, (e) a fourth means for calculating a temperature correction coefficient following the foregoing electrical quantity which is proportional to the foregoing internal resistance of the sensor, and (f) a fifth means for applying correction to the measured amount of the limiting current which is determined by means of the second means receiving the output of the fourth means.

The above and other objects, advantages and features of this invention will become apparent from the following description of the foregoing and other embodiments thereof presented in conjunction with the accompanying drawings.

DETAILED DESCRIPTION

Figure 1A:
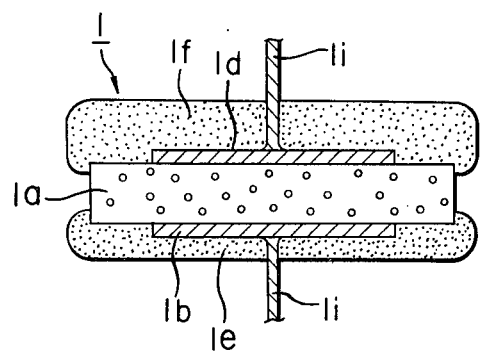
FIG. 1A is a cross sectional view of an exemplary configuration of a limiting electric current type oxygen concentration sensor.

FIG. 1A shows an example of the configuration of a limitint current type oxygen concentration sensor which is employed for the present invention. Referring to the figure, an oxygen ionic conductor $1a$ is a plate or a cylinder of which the material is a dense sintered body of a solid solution containing zirconia ($ZrO_2$) and one or more materials selected from the group including $Y_2O_3$, $Yb_2O_3$, $Gd_2O_3$, MgO, CaO, $Sc_2O_3$ et al. which function as a stabilizer or a solid solution containing $Bi_2O_3$ and one or more materials selected from the group including $Y_2O_3$, $Er_2O_3$, $WO_3$ et al. which function as stabilizer, or a solid solution containing one or more materials selected from $HfO_2$, $ThO_2$ etc. and one or more materials selected from the group including CaO, MgO, $Y_2O_3$, $Yb_2O_3$ et al. which function as a stabilizer. An anode $1b$ is placed along one surface of the foregoing oxygen ionic conductor $1a$, and a cathode $1d$ is placed along the other surface of the oxygen ionic conductor $1a$. The anode $1b$ and cathode $1d$ face each other. The electrodes, the cathode $1d$ and the anode $1b$, are produced of a thermo-resistant electron conductor which is a substance selected from the group of Pt, Ag, Rh, Ir, Pd et al. or is an alloy containing one or more of the foregoing metals. Employment of these materials enables the amount of electrode interface resistance which appears between the oxygen ionic conductor $1a$ and either of these electrodes $1b$ and $1d$ to be decreased. The foregoing cathode $1d$ is covered with a material having perforations. FIG. 1A shows a schematic configuration of an example of the limiting current type oxygen concentration sensor in accordance with an embodiment of this invention, the sensor being provided with a porous layer $1f$ which covers the electrode $1d$. This porous layer $1f$ functions to limit the quantity of oxygen gas flowing toward the cathode $1d$. On the other hand, the anode $1b$ is covered with another porous layer $1e$ which functions to protect the anode $1b$ from being contaminated by foreign materials et al. The porous layers $1f$ and 1e are produced of a thermo-resistant inorganic material e.g. alumina, magnesia, silica, spinnel or mullite. It is preferable, that the porous layer 1e has a magnitude of gas permeability which is equal to or larger than that of the porous layer 1f. This is because the porous layer 1f is required to control the quantity of oxygen gas which diffuses from the outside of the porous layer 1f to be supplied to the oxygen ionic conductor 1a through the cathode 1d, albeit the function of the porous layer 1e is limited to allow oxygen gas to drain from the oxygen ionic conductor 1a through the anode 1b.

Each of the electrodes has a lead wire 1i which is produced of a thermo-resistant electronic conductor which is selected from the group of Pt, Ag, Rg, Ir, Pd et al. or an alloy thereof, as is the material of the foregoing electrodes.

Figure 1B:
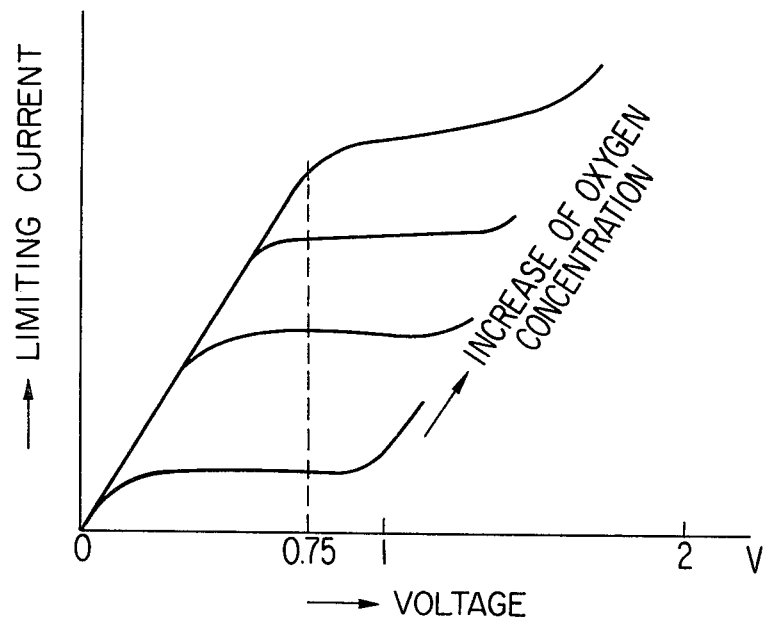
FIG. 1B is a graph showing exemplary characteristics of the voltage vs. current relations of a limiting electric current type oxygen concentration sensor, the graph being shown employing the oxygen concentration as a parameter.

Application of a voltage across the anode 1b and the cathode 1d of a limiting current type oxygen concentration sensor having the foregoing configuration under a condition that a gas of which the oxygen concentration is measured is available surrounding the sensor, causes the cathode 1d to ionize oxygen to convert it to oxygen ions. After passing through the oxygen ionic conductor 1a, the oxygen ions are deionized in the anode 1b. The deionized oxygen i.e. oxygen gas is purged out of the sensor. A potential limitation applied to the quantity of oxygen gas which is supplied to the surface between the cathode 1d and the oxygen ionic conductor 1a causes the corresponding limitation of the quantity of oxygen ions ionized in the cathode 1d. Since this limitation in the quantity of oxygen ions further results in the corresponding limitation for the quantity of electronic charges carried by the oxygen ions (electric current), the intensity of electric current saturates, despite voltage increases. Accordingly, the limiting current characteristics as shown in FIG. 1B are exhibited by the sensor. Therefore, a gradual increase in the voltage applied across the cathode 1d and the anode 1b is accompanied by the corresponding increase in the electric current which increases in proportion to the increase in the voltage until the amont of electric current reaches a saturated value, as shown in FIG. 1B. The voltage range in which a current increases in proportion to an increase in a voltage is defined as the resistance domination range, and the voltage range in which a current is limited or saturates, despite an increase in voltage, is defined as the overpotential control range. The electric current in the foregoing overpotential control range is defined as a "limiting current". This current limiting phenomenon is caused by a phenomenon in which the difference of oxygen concentration in and out of such an oxygen diffusion limiter as described above becomes almost equal to the amount of the oxygen concentration outside the oxygen diffusion limiter.

As presented in the foregoing description, this disclosed example refers to a sensor in which a porous layer is used for realization of the foregoing oxygen diffusion limiter. Incidentally, however, equipment in accordance with the present invention which will be described below, also allows an oxygen concentration sensor in which a cathode itself is used as an oxygen diffusion limiter.

In the resistance domination range, a voltage/current ratio is predominantly determined by the sum of the amounts of the internal resistance of the oxygen ionic conductor and the electrode resistance appearing between the oxygen ionic conductor and the electrodes.

In a voltage range in which the amount of voltage exceeds the voltage of the overpotential control range, a voltage range is observed in which the amount of electric current sharply increases following an increase of voltage. This sharp increase in the amount of current is caused by a phenomenon in which the quantity of oxygen available in the neighborhood of the oxygen ionic conductor increases, because the voltage applied across the electrodes in the amount exceeding the limit causes portions of carbon dioxide ($CO_2$) and water vapor ($H_2O$) contained in the exhaust gas to decompose and to produce oxygen gas in the neighborhood of the oxygen ionic conductor. This causes an effect as if the oxygen concentration is increased an the gas whose oxygen concentration is measured. This voltage range is defined as an excess current range. As is clarified in the foregoing description, a lesser magnitude of voltage applied to an oxygen concentration sensor corresponds to resistance domination range and a higher amount of the voltage applied to an oxygen concentration sensor corresponds to the excess current domination range. Therefore, the measurement of a limiting current is required to be carried out in a voltage range between the resistance domination range and the excess current domination range or in the overpotential control range. The magnitude of this overpotential control range is determined following the compositions of a gas and/or of a material of which the electrodes are produced. The exemplary amount of this overpotential control range is approximately 1.3 through 1.6 (V) for an atmosphere containing a high quantity of inert gases e.g. nitrogen, argon et al. and some quantity of oxygen. The corresponding amount for a gas containing a high quantity of carbon dioxide and water vapor and a relatively small quantity of oxygen gas e.g. an exhaust gas is approximately 0.6 through 0.8 (V). Since the maximum amount of the voltage drop generated in the internal resistance of a sensor can be assumed to be approximately 0.5 (V), it is realistic to design the amount of voltage applied across the electrodes in the range of 0.6 through 0.75 (V), for the purpose of avoiding the influence by the internal resistance and/or the excess current.

Figure 2:
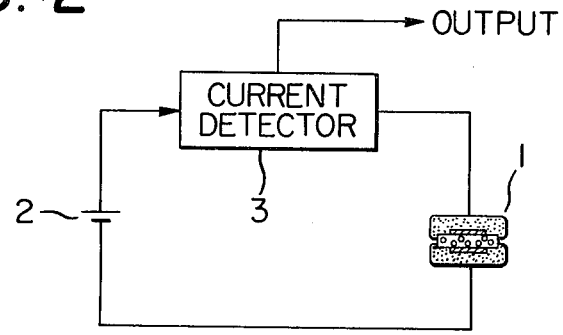
FIG. 2 is a block diagram of one example of circuits which are employed in conjunction with a limiting electric current type oxygen concentration sensor, the circuit being available in the prior art.
Figure 3:
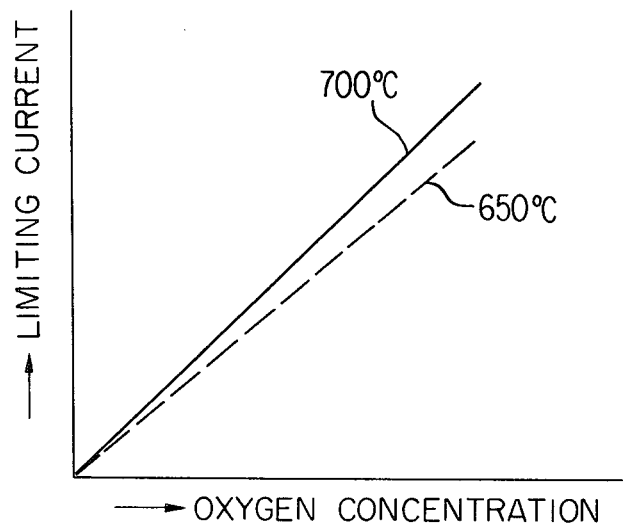
FIG. 3 is a graph showing the oxygen concentration vs. limiting current relations exhibited by a limiting current type oxygen concentration sensor available in the prior art, the graph showing the figures determined under two different temperature conditions.

FIG. 2 shows a block diagram of one example of the circuits which are employed in conjunction with a limiting electric current type oxygen concentration sensor, the circuit being available in the prior art. Referring to the figure, a limiting current generated in a limiting current type oxygen concentration sensor 1 in response to application of a constant voltage supplied by a constant voltage power supply 2 is detected by means of a current detector 3. FIG. 3 is a graph which shows the oxygen concentration vs. limiting current relations inherent in the limiting current type oxygen concentration detector available in the prior art. It is obviously observed in FIG. 3 that accuracy of measurement is unsatisfactory, because oxygen concentration vs. limiting current relations vary according to the temperature of the sensor. Although it is known that a limiting current is not necessarily proportional to the oxygen concentration in a high oxygen concentration range, this unproportionality is ignored.

Figure 4:
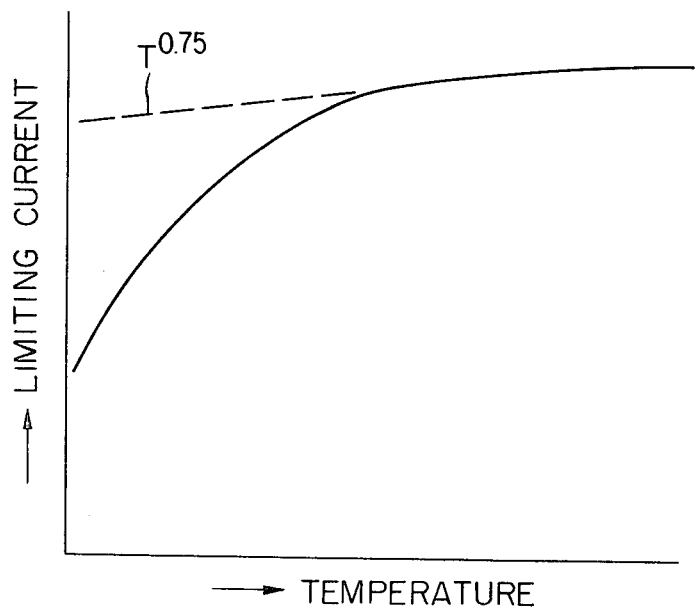
FIG. 4 is a graph showing the temperature vs. limiting current relations under the condition where the oxygen concentration is maintained constant.

FIG. 4 shows the characteristics in which the magnitude of limiting current varies depending on the temperature of the sensor for an arbitrary oxygen concentration. This temperature dependence is mainly caused by the corresponding nature of the diffusion coefficient of a gas.

The characteristics of an oxygen concentration sensor which is provided with a porous layer which functions to regulate the flow quantity of oxygen gas therein is represented by the following formula.

$$Il = \frac{4 \, F \, S \, D_{o2eff} \, P}{R \, Tl} \ln\left(\frac{1}{1 - P_{o2}/P}\right) \tag{1}$$

wherein,
Il represents the limiting current,
F represents Faraday constant
S represents the area of a member which regulates the flow quantity of oxygen gas,
$D_{o2eff}$ represents the effective diffusion coefficient,
$P_{o2}$ represents the partial pressure of oxygen gas,
P represents the total pressure,
R represents a gas constant,
T represents the absolute temperature,
l represents the thickness of a porous layer, and
ln represents natural logarithm.

If the ratio of oxygen partial pressure to the total pressure $P_{o2}/P \ll 1$, the formula (1) can be approximated as $$Il \approx \frac{4 \, F \, S \, D_{o2eff} \, P}{R \, Tl} \, \frac{P_{o2}}{P} \tag{2}$$

From experience, $D_{o2eff}$ is represented by $$D_{o2eff}(T) = D_{o2eff}(T_o) \left(\frac{T}{T_o}\right)^{m+1} \tag{3}$$

wherein,
To represents reference temperature,
$D_{o2eff}(T)$ represents the effective diffusion coefficient at the temperature T,
$D_{o2eff}(T_o)$ represents the effective diffusion coefficient at the temperature To.

It is known that the exponent (m+1) is approximately equal to 1.75 in the foregoing formula (2).

Accordingly, the ratio of Il(T) which is the output current at the temperature T to Il(To) which is the output current at the temperature To in the same partial pressure of oxygen gas or the temperature dependence of an output current is represented by $$\frac{Il(T)}{Il(T_o)} = \left(\frac{T}{T_o}\right)^m \tag{4}$$

If the temperature dependence of a limiting current is limited to the temperature dependence caused by a variation of the diffusion coefficient of a gas following a variation of temperature, the limiting current of a sensor varies approximately in proportion to the variation of temperature, as shown by a broken line in FIG. 4. And, the proportion constant is small ($T^{0.75}$). In reality, however, a sharp decrease of a limiting current is often observed as shown in solid line in FIG. 4. This is caused by a large amount of voltage-drop which is caused by a substantial increase in the internal resistance in a low temperature range. It would be possible to eliminate the adverse effect of the temperature dependence of a sensor, if the temperature of the sensor is maintained constant. However, it is clear that this requires various components including a temperature detector, a heater, a temperature regulator et al. and that an oxygen concentration detector based on this requirement is involved with various problems e.g. complicated construction, expensive production costs, higher power consumption etc.

The object of the present invention is to provide a limiting electric current type oxygen concentration detector wherein the foregoing drawbacks are removed even under the condition that the detector is employed at a varying temperature rather than being employed at a regulated temperature.

Figure 5:
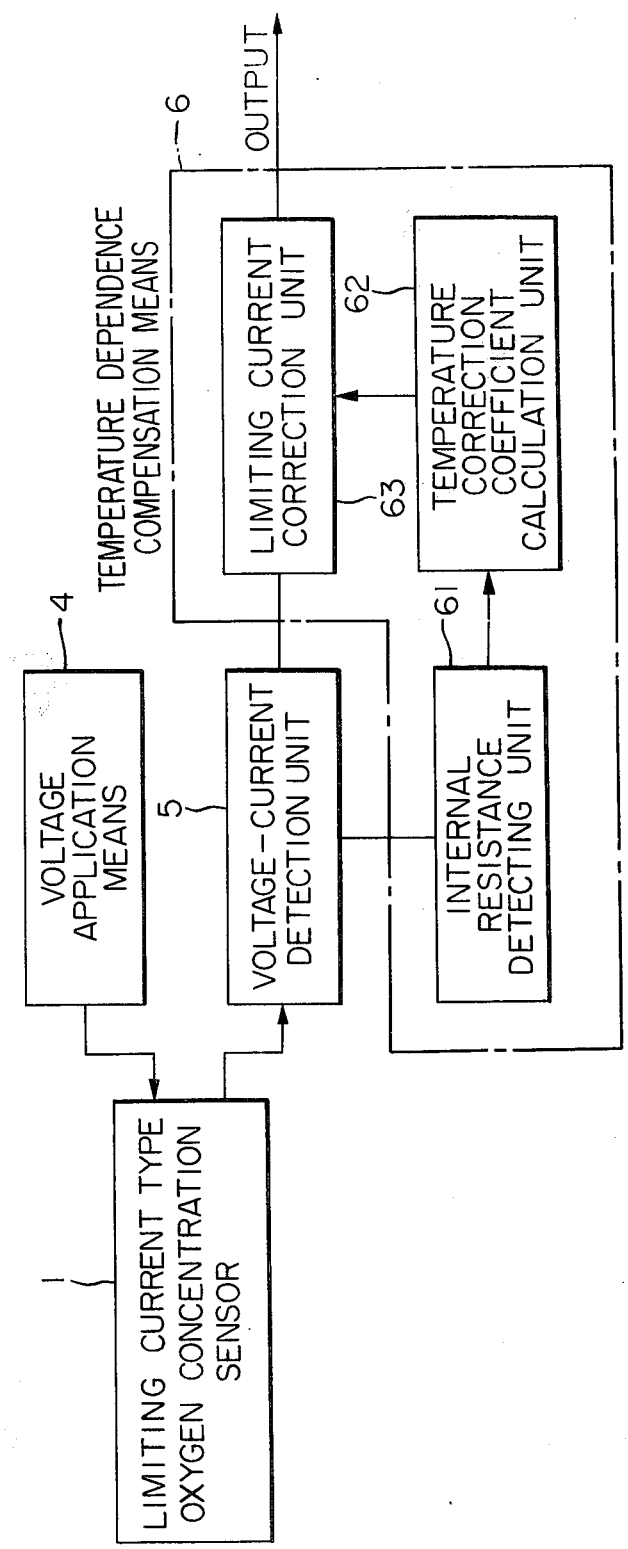
FIG. 5 is a block diagram showing a fundamental configuration of a limiting current type oxygen concentration detector in accordance with the present invention.
Figure 6A:
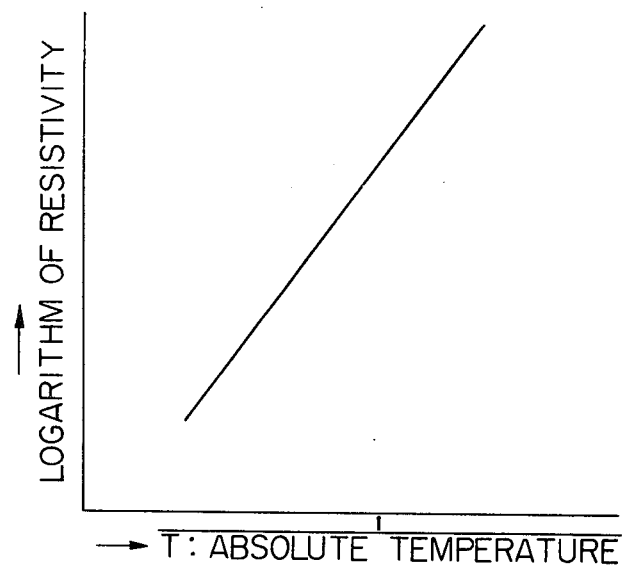
FIG. 6A is a graph showing the temperature vs. internal resistance relations of a sensor which represents the nature of the internal resistance of a sensor whose resistivity varies with temperature.
Figure 6B:
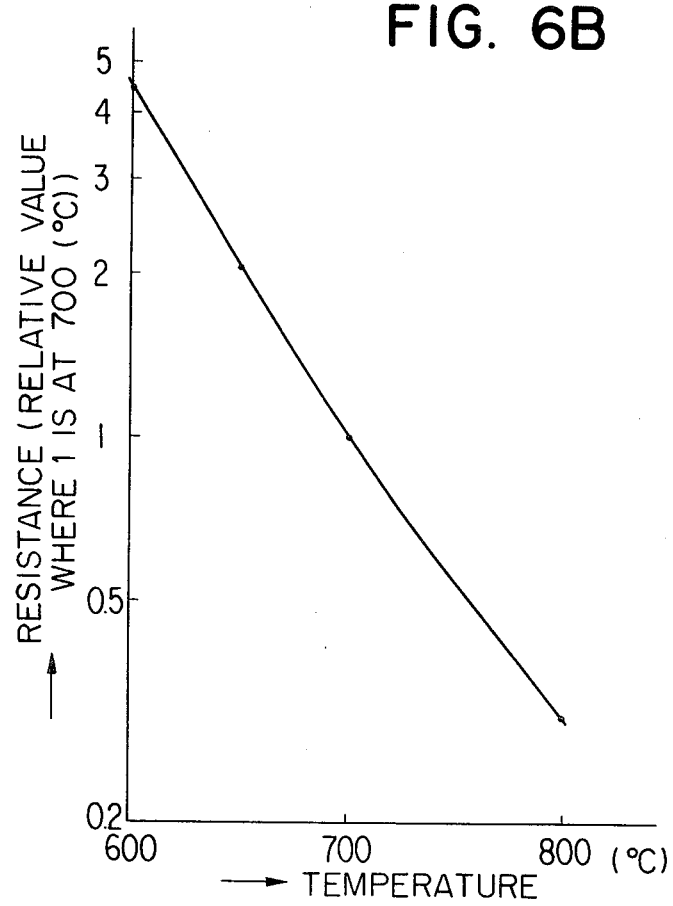
FIG. 6B is a graph showing the temperature vs. internal resistance relations of a sensor which represents the nature of the internal resistance of a sensor internal resistance varies with temperature.

FIG. 5 is a block diagram showing the fundamental configuration of a limiting electric current type oxygen concentration detector in accordance with the present invention. Referring to FIG. 5, the detector is provided with a limiting current type oxygen concentration sensor 1, a means for applying voltage 4 which is a means for alternating application of two types of voltage including (1) a voltage for detecting a limiting current flowing in the sensor and (2) a voltage (or a current) for detecting an internal resistance of the sensor 1, a means for detecting voltage-current 5 which is a means for detecting a voltage generated by means of application of a voltage supplied by the means for applying voltage 4 to the sensor 1 or a current flowing in the sensor 1 caused by application of a voltage supplied by the means for applying voltage 4, and a means for compensation of temperature dependence 6 which is a means for applying temperature compensation to the output of the sensor 1 or the detected limiting current of the sensor 1. The means for compensation of temperature dependence 6 comprises a unit 61 for detecting the internal resistance of a sensor, a unit 62 for calculation of a temperature correction coefficient which is a means for calculating a temperature correction coefficient according to the internal resistance which is detected employing the unit 61 for detecting the internal resistance of a sensor, and a unit 63 for correction of a limiting current which is a means for correcting the amount of the limiting current according to the foregoing temperature correction coefficient. FIGS. 6A and 6B show the relations between the specific resistance $\rho$ of an oxygen ionic conductor composing an oxygen concentration sensor and the temperature of the sensor. A semilogarithmic scale is employed for FIG. 6B.

The specific resistance $\rho$ of an oxygen ionic conductor is represented by the following formula.

$$\rho = c_1 e^{(E/KT)} \tag{5}$$

wherein,
$c_1$ represents a coefficient,
e represents the base of natural logarithm,
E represents activation energy of the oxygen ionic conductor,
K represents Boltzman's constant, and
T represents the absolute temperature of a sensor.

Referring to the formula (5), a coefficient $c_1$ and an activation energy E are parameters determined following the composition of materials with which a sensor is produced, the conditions of sintering applied to the oxygen ionic conductor, impurities contained in the conductor. An oxygen ionic conductor is preferably a solid containing zirconia and one or more of the materials selected from the group including $Y_2O_3$, $Yb_2O_3$, $Gd_2O_3$, MgO, CaO, $Sc_2O_3$ et al. or containing $Bi_2O_3$ and one or more materials selected from the group including $Y_2O_3$, $Er_2O_3$, $WO_3$ et al., because employment of these materials is effective to decrease the amount of the coefficient $c_1$, thereby decreasing the amount of the specific resistance $\rho$. Either of these oxygen ionic conductors is inclined to sharply increase the amount of the specific resistance $\rho$ thereof following a decrease in the temperature thereof, as shown in FIG. 6(b). This is because the amount of the activation energy is high in the magnitude of 0.5 through 1.4 (eV) for those materials. Another kind of resistance is recognized along the interface between an ionic conductor and electrodes, in addition to the internal resistance of an ionic conductor. This interface resistance varies depending on the condition which is determined following the surface treatment of the oxygen ionic conductor, on the composition of the electrode materials and on the other conditions. It is possible to decrease the interface resistance, if some of the foregoing substances described above are employed as a material of the electrodes.

As the internal resistance of a limiting current type oxygen concentration sensor varies depending on the temperature thereof, it is possible to detect the temperature thereof by means of measurement of the internal resistance thereof. Substituting the condition that $\rho = \rho_o$ provided $T = T_o$ into the foregoing formula, $$c_1 = \frac{\rho_o}{e^{(E/KT_o)}} \tag{6}$$

$$\rho = \rho_o e^{\frac{E}{K}\left(\frac{1}{T} - \frac{1}{T_o}\right)} \tag{7}$$

$$T = \frac{1}{K/E \log_e (\rho/\rho_o) + 1/T_o} \tag{8}$$

wherein, $\log_e$ represents the natural logarithm.

Since the amount of the internal resistance of a sensor is practically proportional to the amount of a specific resistance of the material of which the sensor is produced, the formula (8) including specific resistance $\rho$ and $\rho_o$ as the independent variables can be converted to the following formula.

$$T = \frac{1}{K/E \log_e (R/R_o) + 1/T_o} \tag{9}$$

wherein,

R represents the internal resistance of a sensor, and

Ro represents the internal resistance of a sensor at a temperature To.

Since the value of E and the relations and between To and Ro are determined for each specific sensor, the absolute temperature T can be determined according to the internal resistance R.

A correction can be realized by multiplication of a function $$\left(\frac{T}{T_o}\right)^{-m}$$

which brings the error caused by the temperature dependence shown in FIG. 4 to zero to the formula (4). In other words, a temperature correction coefficient $\alpha(T)$ is $$\alpha(T) = \left(\frac{T}{T_o}\right)^{-m} \tag{10}$$

Referring to the block diagram shown in FIG. 5, a unit for calculation of temperature correction coefficient 62 is a means for calculating the temperature correction coefficient $\alpha(T)$, and a correction unit 63 is a means for applying temperature correction to the output of the means for detecting voltage/current 5 by means of multiplication of the temperature correction coefficient $\alpha(T)$ by the output of the means for detecting voltage/current 5.

In the foregoing manner, it is possible to eliminate the temperature dependent component from the formula (4) which includes a component which depends on temperature. In other words, multiplication of the temperature correction coefficient $\alpha(T)$ to the formula (4) results in elimination of a temperature dependent component. As a result, a limiting current which is proportional exclusively to the partial pressure of oxygen can be calculated.

A means by which a temperature resistance coefficient $$\alpha(T) = \left(\frac{T}{T_o}\right)^{-m}$$

is calculated from the internal resistance of a sensor will be described below.

Substituting the formula (9) in the formula (10), $$\alpha(T) = \left(\frac{T}{T_o}\right)^{-m} = \left\{\frac{KT_o}{E} \log_e \left(\frac{R}{R_o}\right) + 1\right\}^m \tag{11}$$

Either hardware or software can be employed for calculation of the formula (11) to acquire a temperature correction coefficient and for multiplication of the temperature correction coefficient by the amount of limiting current which is detected by means of the means for detecting voltage/current 5. However, since the formula (11) contains logarithmic and power calculations, the calculation is rather complicated.

If simplicity supersedes accuracy, it is possible to employ an approximation formula to be described below.

Firstly, the following formula simplifies the logarithmic calculation term.

$$\left(\frac{T}{T_o}\right)^{-m} \approx \left\{\frac{KT_o}{E}\left(2 \cdot \frac{R/R_o - 1}{R/R_o + 1}\right) + 1\right\}^m \tag{12}$$

Secondly, the following formula simplifies the power calculation.

$$\left(\frac{T}{T_o}\right)^{-m} \approx 1 + 2m \frac{KT_o}{E} \cdot \frac{R - R_o}{R + R_o} \tag{13}$$

Figure 7:
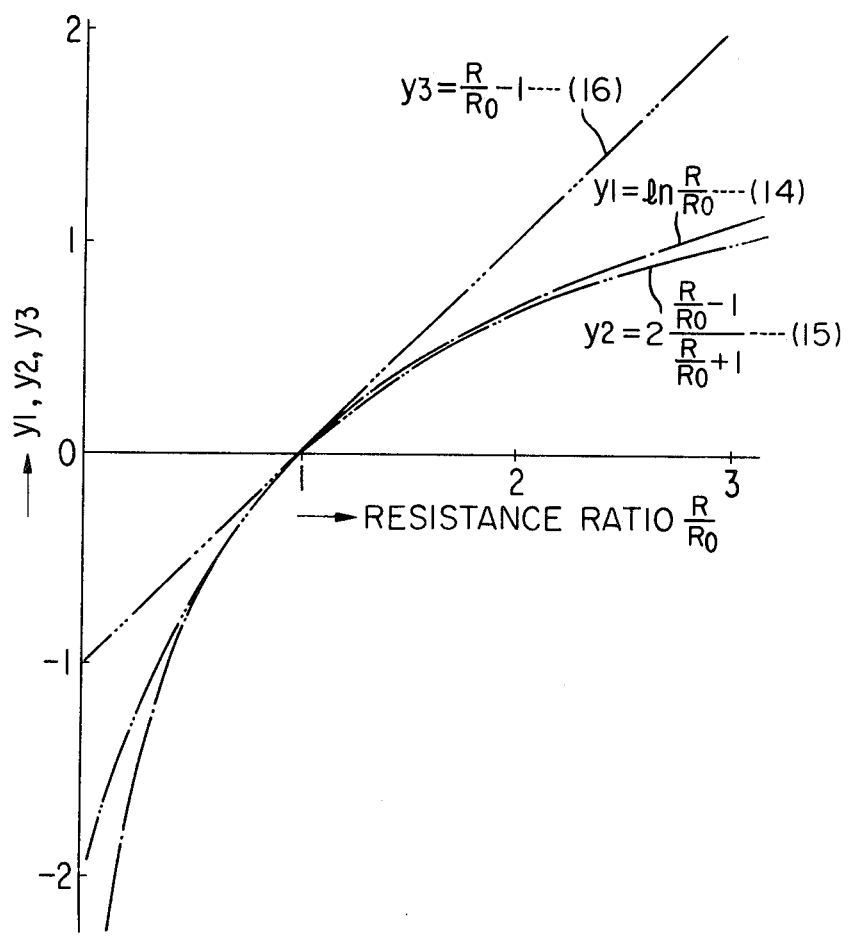
FIG. 7 is a graph showing the degree of accuracy involving two independent approximation formulae and the range to which the foregoing approximation formulae are allowed to be applied.

FIG. 7 compares the accuracy of two independent approximation formulae which are applicable to $$y_1 = \log_e \frac{R}{Ro} \tag{14}$$

for the ultimate purpose to determine the applicable range in terms of R/Ro of the two formulae. In other words, the formula 14 can be approximated by $$y_2 = 2\left(\frac{R/Ro - 1}{R/Ro + 1}\right) \tag{15}$$

or $$y_3 = \frac{R}{Ro} - 1 \tag{16}$$

The figure shows a good conformity for the formula (15) in the range of $0.3 < (R/Ro) < 3$. The figure also shows a good conformity for the formula (16) in the range of $0.6 < (R/Ro) < 1.4$ which is relatively narrower than for the formula (15). A later description will prove that even the formula (16) is satisfactory for the purpose to realize the temperature compensation.

Further, a power calculation formula $$Z_1 = (1+x)^m \tag{17}$$

can be approximated by $$Z_2 \doteq 1 + mx \tag{18}$$

Since the amount of x is much less than 1 in the temperature range, 600° through 1,000° C., at which this sensor is employed, those formulae can be approximated with an error range less than 1 (%). Following the approximation formula (16), $$\left(\frac{T}{To}\right)^{-m} \approx 1 + m\frac{KTo}{E}\left(\frac{R}{Ro} - 1\right) \tag{19}$$

is satisfied.

The foregoing simplification excludes logarithmic and power calculations from the formula (11), leaving addition, subtraction, multiplication and division for the formula (13) and addition and subtraction for the formula 19. This is effective to simplify the construction of the calculation means and to decrease the production cost thereof.

It is possible to employ thermo-sensitive elements e.g. a thermistor or a thermocouple for measurement of the temperature of a sensor rather than employing a method wherein the temperature of a sensor is assumed to follow the internal resistance thereof.

Figure 8:
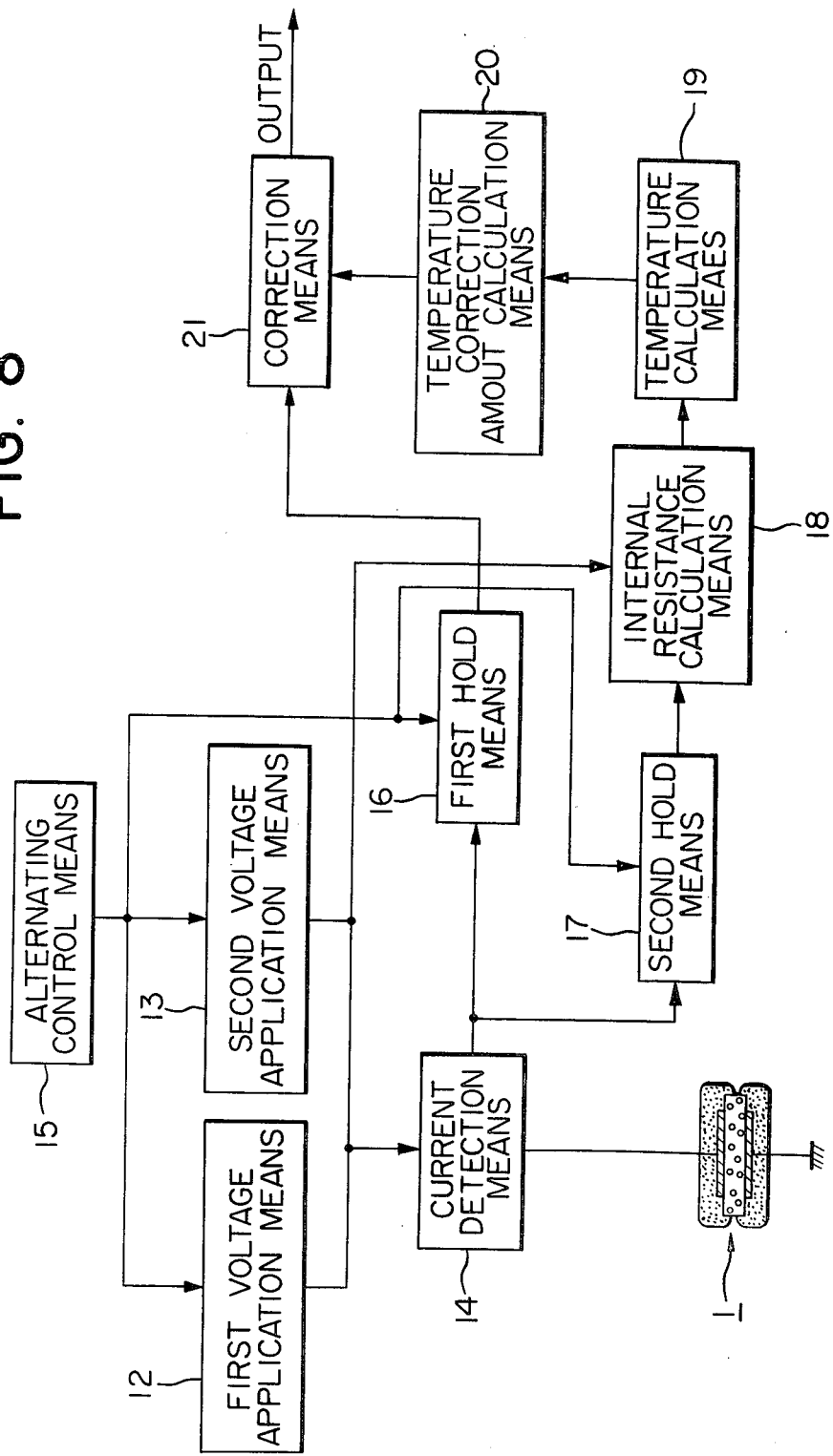
FIG. 8 is a block diagram of a limiting current type oxygen concentration detector in accordance with one embodiment of the present invention.

FIG. 8 shows the conceptual configuration of a limiting current type oxygen concentration detector in accordance with one embodiment of the present invention, wherein a time sharing system is employed for alternative measurement of a limiting current of an oxygen concentration sensor which composes the oxygen concentration detector and of the temperature of the sensor (which is measured by means of measurement of the internal resistance of the sensor).

Referring to the figure, a limiting current type oxygen concentration sensor 1 has a conceptual configuration identical to that of the sensor shown in FIG. 1A. A first voltage application means 12 which applies voltage to the sensor 1 during a first period for the purpose to measure a limiting current of the sensor 1 and second voltage application means 13 which applies voltage to the sensor during a second period for the purpose to measure the internal resistance of the sensor 1 are connected to the sensor 1 through a current detection means 14. The output terminal of the current detection means 14 is connected to the input terminals of a first hold means 16 which functions to hold or memorize the information representing the amount of limiting current which was detected in the latest first period and of a second hold means 17 which functions to hold or memorize the information representing the amount of current which corresponds to the internal resistance of the sensor which was detected in the latest second period. An alternating control means 15 is connected to the first voltage application means 12, the second voltage application means 13, the first hold means 16 and the second hold means 17 to control each of them. The output terminals of the second voltage application means 13 and the second hold means 17 are connected to the input terminal of an internal resistance calculation means 18. The internal resistance calculation means 18 functions to calculate the internal resistance of the sensor 1 based on the relations between the voltage applied to the sensor 1 and the current flowing in the sensor 1 responsive to the voltage applied to the sensor 1. The output terminal of the internal resistance calculation means 18 is connected to the input terminal of a temperature calculation means 19, which calculates the temperature of the sensor 1 based on the internal resistance of the sensor 1 employing the relations shown in the formula (11). The output terminal of the temperature calculation means 19 is connected to the input terminal of a temperature correction amount calculation means 20, which calculates the temperature correction amount employing the relations shown in the formula (12). The output terminal of the first hold means 16 which holds the information regarding the limiting current is connected to one of the input terminals of a correction means 21, and the output terminal of the temperature correction amount calculation means 20 is connected to the other of the input terminals of the correction means 21. The correction means 21 functions to apply temperature correction to the detected amount of limiting current.

The function of the circuit shown in FIG. 8 and the preferable conditions which allow normal function for the circuit shown in FIG. 8 will be described below. Since the first voltage application means 12 is required to output a voltage which is suitable for measurement of a limiting current of the sensor, the voltage is preferably selected to be close to the maximum end of the overpotential control range which corresponds to the oxygen concentration of a gas whose oxygen concentration is measured, albeit attention must be paid also to the oxygen concentration measurement range, the concentration of combustion products, the composition of the electrodes etc. for selection of the preferable amount of voltage. On the other hand, since the second voltage application means 13 is required to output a voltage which is suitable for measurement of the internal resistance of the sensor, the voltage must be selected in the resistance domination range which is less (e.g. 0.7 times as high as or less) than the minimum amount in the overpotential control range which corresponds to the oxygen concentration of a gas of which the oxygen concentration is measured, albeit attention must be paid to the employment conditions et al.

The cycle of the alternating control and the ratio with which time is allocated to the first period and the second period are preferable to be selected as described below. The length of the first period is not necessarily required to be equal to that of the second period. In the case of control in an internal combustion engine, the temperature of the exhaust gas is inclined not to change so rapidly in response to a change in the oxygen concentration. Therefore, allocation of a longer time to the first period in which measurement is allowed for the oxygen concentration than to the second period in which measurement is not allowed for the oxygen concentration would further enhance the effects of the present invention. On the other hand, as to the cycle with which the first period and the second period are alternated, a higher cycle is preferable, because it allows a better response for the detector, unless the higher cycle causes a current to be unsuitable to a voltage having the higher cycle. Therefore, the increase in the cycle is limited to the level of 1 (KHz) from this aspect.

The function of the internal resistance calculation means 18 is to detect the voltage output of the second voltage application means 13 during the second period and to divide the amount of the voltage by the amount of current held by the second hold means 17. However, in the case where the amount of the second voltage application means 13 is not variable, it is possible to determine the internal resistance of a sensor employing steps including the calculation of the reciprocal of the current and multiplication thereof by a proportion coefficient. Further, it is possible to determine the internal resistance of a sensor based on the amount of the voltage which is required to flow a constant amount of current to the sensor.

The function of the temperature calculation means 19 is to calculate the amount of temperature of a sensor based on the resistance, employing the formula (13).

The function of the temperature correction amount calculation means 20 is to carry out the calculation of the formula (11) or to carry out the calculation of the reciprocal of the temperature dependence of a sensor shown in FIG. 4. The correction means 21 multiplies the limiting current by a temperature correction coefficient.

FIG. 8 shows a circuit in which the output of the current detection means 14 is applied to the input terminal of the first hold means 16, the first hold means 16 is allowed to hold the information representing the limiting current to which temperature correction has been applied. FIG. 8 shows a circuit in which the output of the current detection means 14 is also applied to the input terminal of the second hold means 17. The second hold means 17 is allowed to hold the output of the internal resistance calculation means 18.

Albeit FIG. 8 shows a circuit provided with two independent voltage application means 12 and 13, these two means 12 and 13 can be replaced by one rectangular wave oscillator.

A circuit for calculation of $\log_e (R/R_o)$ shown in the first term of the right side of the formula (11) can be composed of one or more logarithm conversion modules No. 4366 (or 4367) produced by Teledyne Philbrick or the like.

A circuit for power calculation shown on the right side of the formula (11) can be readily composed of one or more power function modules No. 4311 produced by Teledyne Philbrick or the like.

Figure 9:
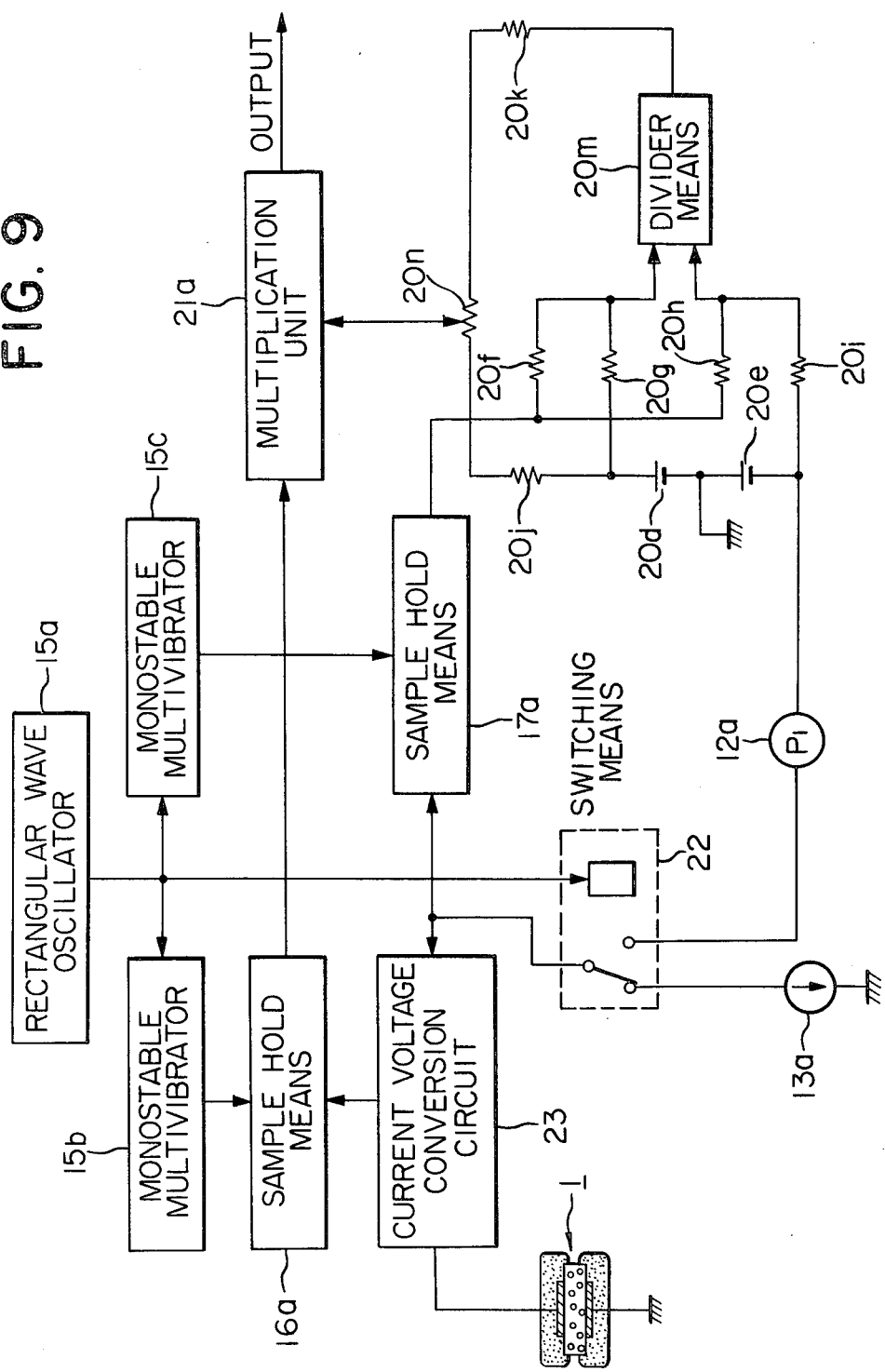
FIG. 9 is a block diagram of a limiting current type oxygen concentration detector in accordance with another embodiment of the present invention.

FIG. 9 shows the circuit of a limiting current type oxygen concentration detector in accordance with another embodiment of the present invention.

Referring to the figure, numeral 1 is a limiting current type oxygen concentration sensor identical to that which is employed for the embodiment shown in FIG. 8. A potentiometer 12a is provided for applying a voltage to the sensor 1 during the first period for the purpose to measure a limiting current. A fixed current supply unit 13a supplies a marginal amount of current to the sensor 1 during the second period for the purpose to measure the internal resistance of the sensor 1. A switching means 22 changes over the voltage and current between the first period and the second period. Numeral 23 is a current voltage converter. A rectangular wave oscillator 15a provides a frequency with which the first period and the second period are changed over. A monostable multivibrator 15b provides a timing at which a limiting current is measured in a limited period of the fixed period in which the limiting current is under a stable situation after a transient phenomenon is over. Numeral 16a is a sample hold means which holds information regarding the limiting current of the sensor 1 for the purpose to avoid discontinuation of supply of the information during the second period in which measurement is not allowed for a limiting current of the sensor 1. A monostable multivibrator 15c provides a timing at which the internal resistance is measured in a limited period of the second period in which the internal resistance of the sensor 1 is under a stable situation after a transient phenomenon is over. Numeral 17a is a sample hold means which holds information regarding the internal resistance of the sensor 1 for the purpose to avoid discontinuation of supply of the information during the first period in which measurement is not allowed for the internal resistance of the sensor 1.

The feature of this embodiment is that a current having a fixed value is supplied to the sensor 1 by the fixed current supply unit 13a during the second period, rather than supplying varying voltage to the sensor 1 during the same period. In this case, since a voltge whose value is proportional to the internal resistance is detected, this voltage is fed to the sample hold means 17a. In comparison with the previous embodiment, this embodiment, is more advantageous, because the configuration is simpler due to the elimination of the internal resistance calculation means 18.

For the purpose of improving the degree of approximation of formula (14), this embodiment is provided with a circuit consisting of two fixed voltage power supplies 20d and 20e, six resistors 20f, 20g, 20h, 20i, 20j and 20k, a divider means 20m and a potentiometer 20n. Measurement is allowed for various sensors having different amounts of temperature coefficient by means of adjustment of the potentiometer 20n.

The function of this circuit shown in FIG. 9 and the preferable conditions which allows normal function for this circuit will be described below. Since the output voltage of the potentiometer 12a, is required to be suitable for measurement of a limiting current of a sensor, the voltage is preferably selected to be 0.25 through 1.5 (V). From a realistic viewpoint, however, a preferable amount of the voltage is approximately 0.75 (V) for the purpose of measuring the oxygen concentration contained in the exhaust gas of an internal combustion engine. On the other hand, since the output current of the fixed current supply unit 13a is required to be suitable for measurement of the internal resistance of the sensor, the current must be selected to generate a voltage-drop in the range of 1 (V) through 0.1 (V). In the case where the measurement is limited a higher oxygen concentration range, the resistance domination range is widened. Therefore, it is preferable that the amount of the current which is supplied to a sensor for the purpose of measuring the internal resistance of the sensor is increased to an amount which is 0.7 times as high as the amount of the voltage in the resistance domination range, following the increase of the resistance domination range. The waveform of the rectangular waves is not required to be identical to each other for the first period in which a limiting current is measured and for the second period in which the internal resistance is measured. Since the speed at which the temperature of a sensor changes is slower than the corresponding speed at which the oxygen concentration changes, allocation of a longer time to the first period in which measurement is allowed for the oxygen concentration than to the second period in which measurement is not allowed for the oxygen concentration would further enhance the effects of the present invention. On the other hand, a cycle in which the first period and the second period are alternated is preferably higher, because a higher cycle allow a better response for the detector. However, if the cycle is too high, the transient period may not terminate, before the next cycle commences, resulting in no time for the measurement. From this viewpoint, the increase in the frequency is limited to the level of 1 (KHz).

The length of the transient period in which no measurement is allowed varies depending on the shape, dimension, material etc. of a limiting current type oxygen concentration sensor. A preferable frequency range is 1 (Hz) through 1 (KHz). For a sensor which exhibits transiency of 5 (ms), the preferable frequency is approximately 100 (Hz).

A combination of the fixed voltage power supply $20d$ and resistors $20f$ and $20g$ satisfies the requirements for approximate calculation of $(R+R_o)$ included in the formula (13). A combination of the fixed voltage power supply $20e$ and resistors $20h$ and $20i$ satisfies the requirements for approximate calculation of $(R-R_o)$ included in the formula (13). The divider means $20m$ carries out a division of $$\frac{R - R_o}{R + R_o}$$

included in the formula (13). A combination of the fixed voltage power supply $20d$, the resistor $20j$, the potentiometer $20n$ and the resistor $20k$ functions to approximately calculate $$\left(1 + 2m\frac{KT_o}{E} \cdot \frac{R - R_o}{R + R_o}\right)$$

included in the formula (13).

The foregoing network consisting of resistors can be replaced by one or more adders to improve the accuracy in calculation.

A temperature correction coefficient obtained by calculation of the formula (13) is fed to a multiplication unit $21a$ which applies temperature compensation to a limited current following the temperature correction coefficient. The potentiometer $20n$ can be adjusted for a sensor having a different amount of temperature coefficient. Albeit FIG. 9 shows that a voltage drop generated in the sensor 11 is the input signal of the sample hold means $17a$, this input signal can be replaced by the output of the divider means $20m$ or even of the temperature correction circuit. Although the output of the current voltage conversion circuit 23 is the input signal of the sample hold means $16a$, this input signal can be replaced by a limiting current applied with temperature correction. It is possible to employ a method in which the output waveform of a sine wave oscillator is reformed by means of a voltage limiter et al. rather than a method employing a rectangular wave oscillator.

It is possible to employ some other means e.g. a thermocouple, a thermo-sensitive resistor (thermistor) and the like rather than a method based on the internal resistance, for the purpose to measure the temperature.

Multivibrators can be replaced by other delay elements.

Figure 10:
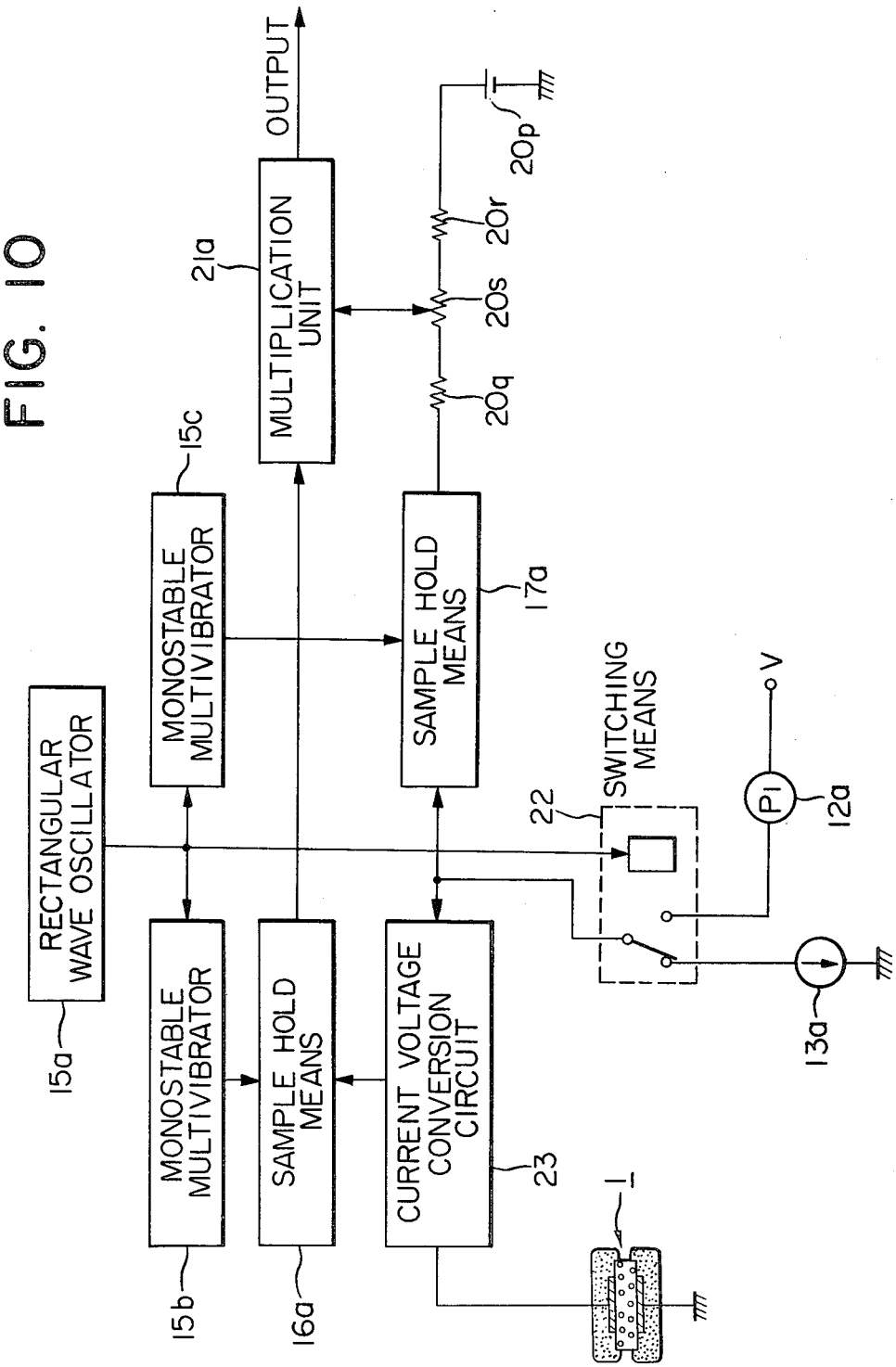
FIG. 10 is a block diagram of a limiting current type oxygen concentration detector in accordance with the third embodiment of the present invention.

FIG. 10 shows the circuit of a limiting current type oxygen concentration detector in accordance with the third embodiment of the present invention. The major difference between this circuit and the circuit shown in FIG. 9 is that this circuit is provided with a temperature correction calculation unit based on the formula (20). Namely, the requirements for calculation of the temperature correction term are satisfied by means of potential dividing employing a combination of a fixed voltage application unit $20p$, resistances $20q$ and $20r$ and a potentiometer $20s$. As a result, the configuration of a temperature correction amount calculation unit is simplified in this circuit. Adjustment is required for a fixed voltage application unit $20p$, if a sensor is replaced by another having a different temperature coefficient.

Figure 11:
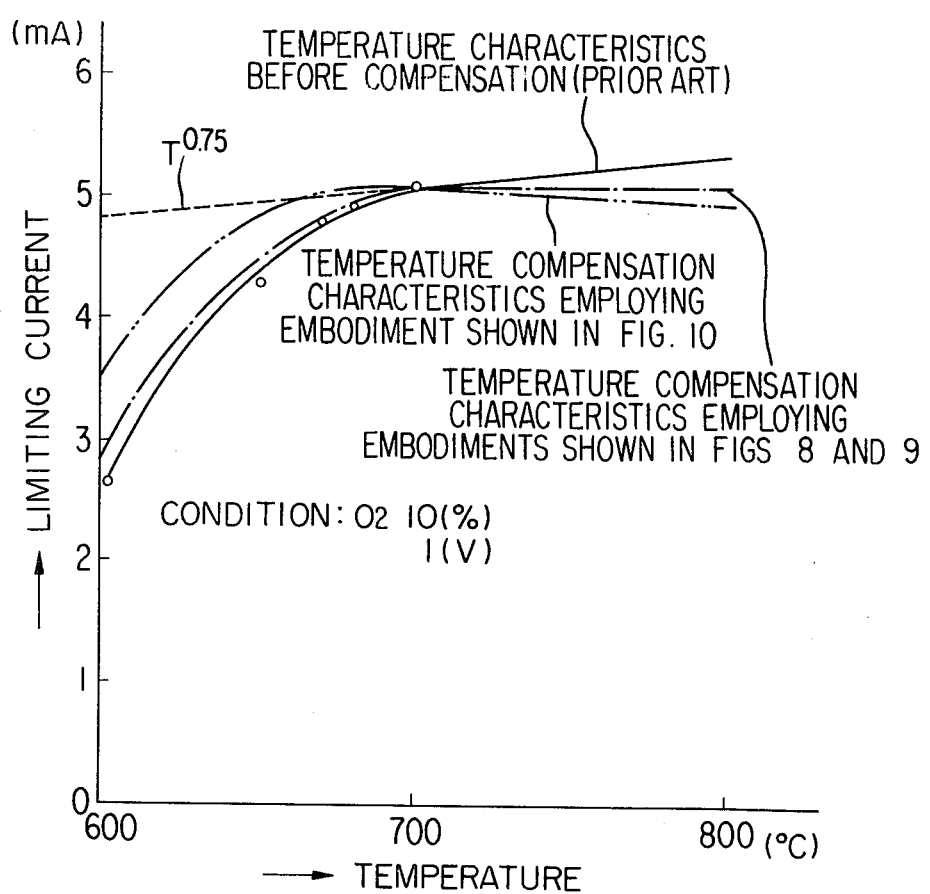
FIG. 11 is a graph showing the temperature vs. limiting current characteristics of various limiting current type oxygen concentration detectors available in the prior art and in accordance with various embodiments of the present invention.

FIG. 11 compares the temperature vs. limiting current characteristics for the various limiting current type oxygen concentration detectors, to demonstrate the effects of the present invention. Referring to FIG. 2 the detector available in the prior art exhibits a considerable magnitude of temperature dependence. This parameter causes an adverse effect for the accuracy and the temperature range in which the measurement is allowed. On the other hand, the detectors in accordance with each embodiment of the present invention show a considerable magnitude of improvement applied to the accuracy and the temperature range in which the measurement is allowed. These improvements are realized by application of temperature compensation.

Even in the case of the simplified configuration shown in FIG. 10, satisfactory results are recognized in comparison with the case in which the accurate temperature compensation system is employed. As shown in FIG. 7, the approximation formula (16) does not satisfactorily approximate the logarithmic calculation formula (14) in the ranges of $0.6 > R/R_o$ and of $R/R_o > 1.4$. Despite this inherent limitation of the approximation formula (16), an embodiment employing the approximation formula (16) exhibits a satisfactory result in comparison with the embodiment employing the formula (14) shown in FIG. 8 or with the embodiment employing the formula (15) shown in FIG. 9. This is because the limiting current type oxygen concentration sensor has an inherent nature that a limiting current sharply decreases in a low temperature range as shown by full lines in FIG. 4 rather than as shown by broken lines in FIG. 4 representing an ideal case. In other words, based on this inherent nature, adjustment is applied to the formula (16) to apply a larger amount of correction to a limiting current for making a larger deviation from the logarithmic function in a low temperature range and to keep it as a logarithmic function in a higher temperature range. The multiplication unit 21a employed for the embodiments shown in FIGS. 9 and 10 can be replaced by an element whose internal resistance is regulated by a gate input voltage of a field effect transistor etc.

The foregoing description has clarified that the limiting electric current type oxygen concentration detector in accordance with the present invention is based on the concept that (a) a limiting current of a sensor is measured in the overpotential control range which is one of the two voltage ranges available for the sensor and the internal resistance of the sensor is measured in the resistance domination range which is the other of the two voltage ranges available for the sensor, (b) the temperature of the sensor is measured following the measurement of the internal resistance and, (c) the errors contained in the limiting current due to the temperature dependence are corrected according to the temperature of the sensor, (d) thereby making it possible to measure the magnitude of limiting current which precisely represents the amount of oxygen concentration. As a result, the accuracy is improved and the temperature range in which the measurement is permitted is expanded for a limiting current type oxygen concentration device.

Although the present invention has been described with reference to specific embodiments, this description is not meant to be construed in a limiting sense. Various other embodiments and/or modifications of the present invention will become apparent to persons skilled in the art upon reference to the description of the present invention. It is therefore contemplated that the claims will cover any such embodiments and/or modifications as fall within the true scope of the present invention.

What is claimed is:

1. A limiting electric current type oxygen concentration detector comprising:
    (a) a limiting electric current type oxygen concentration sensor comprising;
        an oxygen ionic conductor having opposite surfaces,
        a cathode placed on one surface of said oxygen ionic conductor, and an anode placed on the other surface of said oxygen ionic conductor to supply a predetermined voltage,
        a member covering at least the surface of said cathode to regulate the quantity of oxygen gas which diffuses toward said cathode,
    (b) a first means including first and second power supply means for respectively electrically driving said limiting electric current type oxygen concentration sensor, the first power supply means producing limiting current flow in said sensor, said second power supply means producing current flow in said sensor in a resistance domination range thereof in which current flow is proportional to the internal resistance of the sensor,
    (c) a second means for detecting the magnitude of said limiting current flow in said sensor and an electrical quantity which is proportional to the magnitude of said internal resistance,
    (d) a third means for alternately connecting said first and second power supply means to said sensor for respective first and second periods of time, said second means measuring limiting current in said sensor during said first period of time and measuring said electrical quantity during said second period of time which is a measure of the internal resistance of the sensor,
    (e) a fourth means connected to the output of the second means for producing an output signal representing a temperature correction coefficient from the formula $$\alpha T = \left( \frac{T}{T_o} \right) - m$$

based on said electrical quantity, and
    (f) a fifth means connected to said second means and said fourth means for multiplying the output of the second means indicating limiting current of the sensor by the output α(T) of the fourth means.

2. A limiting electric current type oxygen concentration detector defined in claim 1 wherein said first and second power supply means respectively comprise separate first and second voltage supplies.

3. A limiting electric current type oxygen concentration detector defined in claim 2, wherein said second means comprises one electric current voltage converter.

4. A limiting electric current type oxygen concentration detector defined in claim 1, wherein said first and second power supply means respectively comprise a first power supply and a second fixed current supply source.

5. A limiting current type oxygen concentration detector defined in claim 1, wherein said second means comprises one electric current detector.

6. A limiting electric current type oxygen concentration detector defined in claim 1, wherein said second means comprises a first hold means which holds the magnitude of the limiting electric current which was detected during the latest one of said first periods and a second hold means which holds the magnitude of said electrical quantity which was detected during the latest one of said second periods.

7. A limiting electric current type oxygen concentration detector defined in claim 6, wherein each of said first and second hold means comprises a sample hold circuit.

8. A limiting electric current type oxygen concentration detector defined in claim 1, wherein said third means comprises:
    (f) a regulation signal generator which generates a regulation signal following which the time is alternatively allocated to said first and second periods,
    (g) a change-over switch which alternatively switches over from said first and second supply means,
    (h) a first monostable multivibrator which is controlled by said regulation signal to produce a timing signal following which the limiting current of said sensor is detected during said first period, and
    (i) a second monostable multivibrator which is controlled by said regulation signal to produce a further timing signal following which the said quantity indicating internal resistance of said sensor is detected during said second period.

9. A limiting electric current type oxygen concentration detector defined in claim 1, wherein said fourth means comprises:
    (j) a first calculation means which adds a fixed amount having a positive signal to said electrical quantity whose magnitude is proportional to said internal resistance, (k) a second calculation means which adds said fixed amount having a negative signal to said electrical quantity whose magnitude is proportional to said internal resistance, and (l) a third calculation means which calculates the ratio of the outputs of said first calculation means and said second calculation means.

10. A limiting electric current type oxygen concentration detector defined in claim 9, wherein said first, second and third calculation means are analog calculators and said first and second calculation means include resistors.

11. A limiting electric current type oxygen concentration detector defined in claim 1, wherein said fourth means comprises an additional means which adds a fixed amount to said electrical quantity whose magnitude is proportional to said internal resistance.

12. A limiting electric current type oxygen concentration detector defined in claim 11, wherein said addition means is an analog adder composed of resistors.

* * * * *